(12) United States Patent
Ricci et al.

(10) Patent No.: US 7,863,352 B2
(45) Date of Patent: *Jan. 4, 2011

(54) POLYMER CONTAINING CALCIUM SULFATE PARTICLES FOR BONE AUGMENTATION

(75) Inventors: John L. Ricci, Middleton, NJ (US); Harold Alexander, Short Hills, NJ (US); Bruce Hollander, Boca Raton, FL (US)

(73) Assignee: Orthogen LLC, Springfield, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/313,453

(22) Filed: Nov. 20, 2008

(65) Prior Publication Data

US 2009/0076188 A1    Mar. 19, 2009

Related U.S. Application Data

(63) Continuation of application No. 10/892,509, filed on Jul. 14, 2004, now Pat. No. 7,488,761, which is a continuation-in-part of application No. 09/918,445, filed on Aug. 1, 2001, now Pat. No. 6,770,695.

(60) Provisional application No. 60/223,624, filed on Aug. 7, 2000.

(51) Int. Cl.
*C08K 9/10* (2006.01)
*C08K 9/04* (2006.01)
*C08K 3/30* (2006.01)
*A61K 6/08* (2006.01)

(52) U.S. Cl. ........................ 523/210; 523/114; 523/115; 424/426; 524/423

(58) Field of Classification Search ................ 523/210, 523/114, 115; 424/426; 524/423
See application file for complete search history.

(56) References Cited

U.S. PATENT DOCUMENTS

| | | | | |
|---|---|---|---|---|
| 5,663,280 A | * | 9/1997 | Ogoe et al. ............. | 528/196 |
| 6,770,695 B2 | * | 8/2004 | Ricci et al. ............. | 524/423 |
| 6,800,671 B1 | * | 10/2004 | Montgomery et al. ..... | 523/105 |
| 2001/0006678 A1 | * | 7/2001 | Takada et al. ........... | 424/460 |

* cited by examiner

*Primary Examiner*—Tae H Yoon
(74) *Attorney, Agent, or Firm*—Melvin K. Silverman; Yi Li

(57) ABSTRACT

Polymer containing calcium sulfate particles as an implant material are provided. The polymer containing calcium sulfate particles include a calcium sulfate compound coated with a therapeutic polymer containing salicylate, with a coating thickness from about 2 μm to about 50 μm. The therapeutic polymer in the particles is in a range from about 0.1% to about 22% (w/w). The resorption of the particles in vivo is from about four weeks to about twenty weeks. The polymer containing calcium sulfate particles can be used as an implant material for bone repairing and bone augmentation.

9 Claims, 6 Drawing Sheets

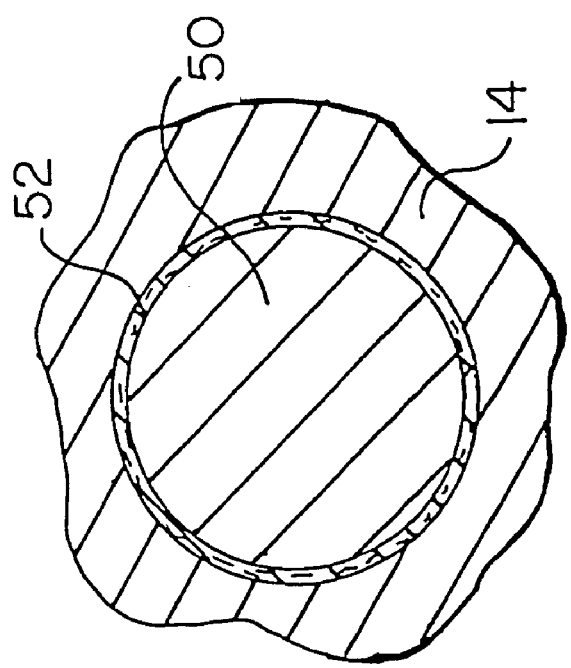
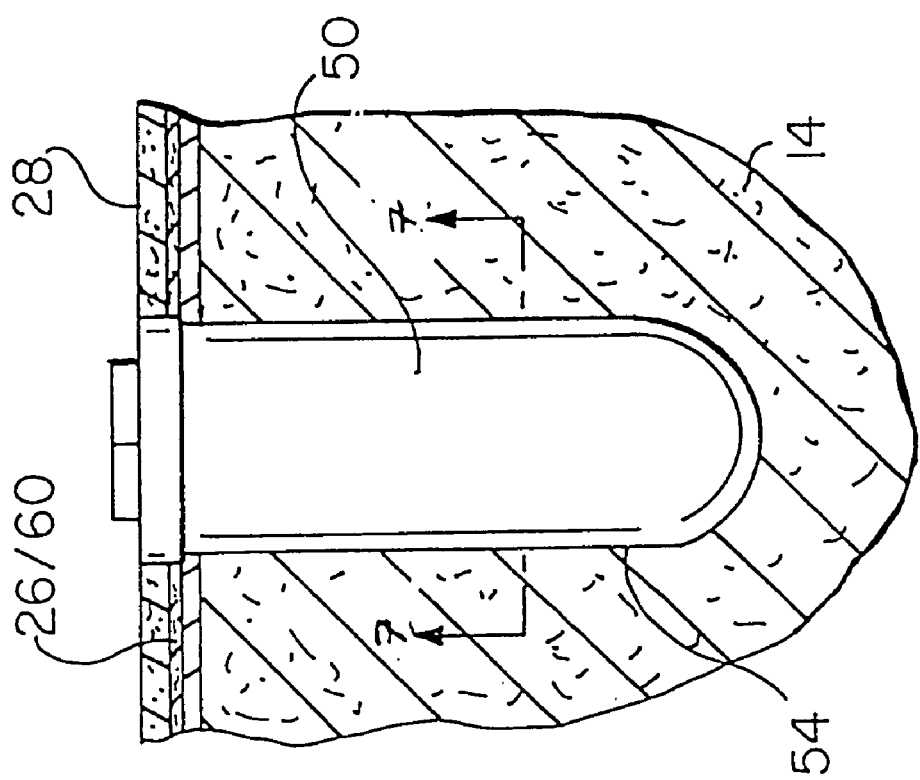

ary applications. In various studies it has been reported that the above-referenced polymers are tissue compatible and they elicit direct bone apposition, particularly with poly(desaminotyrosyl-tyrosine ethyl ester carbonates). However, these
POLYMER CONTAINING CALCIUM SULFATE PARTICLES FOR BONE AUGMENTATION

CROSS REFERENCE TO RELATED APPLICATION

This application is a continuation of patent application Ser. No. 10/892,509, filed on Jul. 14, 2004, now U.S. Pat. No. 7,488,761, which is a continuation-in-part of patent application Ser. No. 09/918,445, filed on Dec. 19, 2001, now U.S. Pat. No. 6,770,695 B2, which claims the benefit under 35 USC 119(e) of the provisional patent application Ser. No. 60/223,624, filed on Aug. 7, 2000. All prior applications are hereby incorporated by reference in their entirety.

BACKGROUND OF THE INVENTION

The repair of bone defects and augmentation of existing bone often require the use of permanent or bio-resorbable materials. Such materials may include autogenous bone graft, allogeneic graft, allogeneic bone graft, or alloplastic materials inclusive of various calcium phosphate ceramics, calcium phosphate cements, calcium sulfate materials, bioglass materials, and composites or other combinations thereof. Calcium sulfate, which is a form of plaster of paris, is a fully bioresorbable material which, for sometime, has been commonly used in cement and pellet form to repair bone defects.

When calcium sulfate is used as a cement to fill a bone void, fracture, or other defect, this material dissolves at a rapid rate, i.e., approximately one millimeter per week from the exterior of the cement towards the center thereof. Research of the present inventors has shown that this material causes precipitation of calcium phosphate deposits as it is resorbed at the surgical site. These precipitates, it has been shown, stimulate and direct the formation of new bone. On the other hand, it is important for purposes of optimal result that calcium sulfate, calcium phosphate, or any other bone repair material stay at the surgical site for a considerable period of time in order to inhibit soft tissue filling of the defect and to stimulate bone repair. However, currently used calcium sulfate materials are resorbed by human bone within two to seven weeks, depending upon the calcium sulfate form and the particular surgical site, which cannot be retained at the site for longer periods. As noted, such material is resorbed faster than it can be replaced by new bone thereby reducing its value to both patient and practitioner.

As such, the principal concern and difficulty expressed by practitioners (such as orthopedics or maxiofacial surgeons) are that calcium sulfate materials bio-resorb or dissolve too rapidly at a surgical or a recipient site, and, thereby, outpace the formation of new bone in human patients. Therefore, a need arises for improved calcium sulfate based compositions which can resorb at the recipient site in a rate desirably matching the rate bone growth.

On the other hand, poly(desaminotyrosyl-tyrosine alkyl ester carbonates, a family of tyrosine-derived polycarbonates, such as poly(desaminotyrosyl-tyrosine ethyl ester carbonates), poly(desaminotyrosyl-tyrosine butyl ester carbonates), poly(desaminotyrosyl-tyrosine hexyl ester carbonates), poly(desaminotyrosyl-tyrosine octyl ester carbonates), are a new class of degradable polymers developed for orthopedic applications. In various studies it has been reported that the above-referenced polymers are tissue compatible and they elicit direct bone apposition, particularly with poly(desaminotyrosyl-tyrosine ethyl ester carbonates). However, these bio-degradable polymers have not been used in combination with calcium sulfate for controlling resorption rate of calcium sulfate in vivo.

SUMMARY OF THE INVENTION

In one aspect, the present invention is directed to implant compositions having controlled resorption rate in vivo for stimulating bone growth, methods of making the implant composition, and kits of implant materials.

In one embodiment, the implant composition comprises a first calcium sulfate compound; polymer containing particles comprising a second calcium sulfate compound, and at least one resorbable polymer of poly(desaminotyrosyl-tyrosine alkyl ester carbonate), and a setting agent for setting the first calcium sulfate compound and the polymer containing particles into a heterogeneous solid composition. The poly(desaminotyrosyl-tyrosine alkyl ester carbonate) includes an alkyl group which has one to ten carbon atoms, such as poly(desaminotyrosyl-tyrosine ethyl ester carbonates), poly(desaminotyrosyl-tyrosine butyl ester carbonates), poly(desaminotyrosyl-tyrosine hexyl ester carbonates), poly(desaminotyrosyl-tyrosine octyl ester carbonates), and derivatives thereof. Upon setting, the first calcium sulfate compound forms a matrix and the polymer containing particles settled within the matrix.

In a further embodiment, the implant composition comprises a calcium sulfate compound; resorbable polymer coated particles; and a setting agent; wherein the resorbable polymer is at least one of poly(desaminotyrosyl-tyrosine alkyl ester carbonate) described above. Upon setting, the calcium sulfate compound forms a matrix and the resorbable polymer coated particles are settled within the matrix.

In another embodiment, the present invention provides a kit of implant materials for bone augmentation and bone defect reparation. The kit comprises dry powder of a first calcium sulfate compound; and polymer containing particles comprising a second calcium sulfate compound and at least one resorbable polymer of poly(desaminotyrosyl-tyrosine alkyl ester carbonate) described above. The kit also comprises a setting agent.

In yet another embodiment, the kit comprises dry powder of a calcium sulfate compound; and resorbable polymer coated particles, wherein said resorbable polymer is at least one of poly(desaminotyrosyl-tyrosine alkyl ester carbonate) described above. The resorbable polymer coated particles comprise a calcium sulfate compound; and a polymer coating with at least one of the resorbable polymer. The kit also comprises a setting agent.

In another aspect, the present invention is directed to polymer containing calcium sulfate particles as an implant material. In one embodiment, the polymer containing calcium sulfate particles include a calcium sulfate compound coated with a therapeutic polymer containing salicylate, with a coating thickness from about 2 μm to about 50 μm. The therapeutic polymer in the particles is in a range from about 0.1% to about 22% (w/w). The resorption of the particles in vivo is from about four weeks to about twenty weeks.

In a further aspect, the present invention is directed to a method of using the implant materials to make the implant composition for bone augmentation and bone defect reparation. The method includes the steps of mixing a calcium sulfate compound and polymer containing particles with a setting agent into a mixture; applying the mixture, either by filling in a recipient site with the mixture, or by coating the mixture on a surface of a surgical implant prior to introducing the surgical implant into the recipient site; and setting the mixture into a heterogeneous solid composition.

The advantages of the present invention will become apparent from the hereinafter set forth Brief Description of the Drawings and Detailed Description of the Invention.

BRIEF DESCRIPTION OF THE DRAWINGS

FIGS. 6 and 7 show a cross-sectional schematic view and a top view, respectively, of the implant composition of the present invention used with a surgical implant which has a smooth exterior surface.

DETAILED DESCRIPTION OF THE INVENTION

Figure 1:
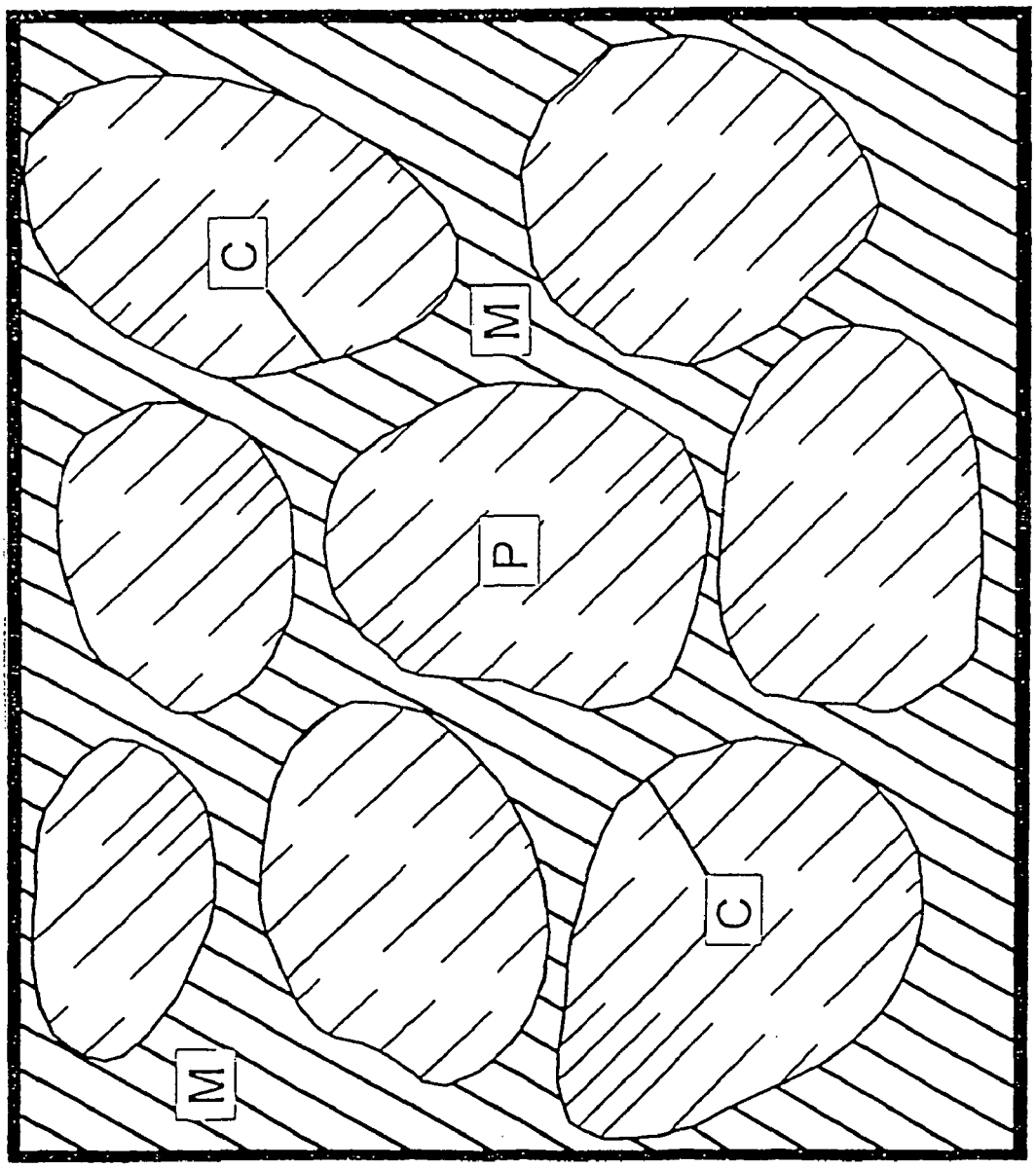
FIG. 1 is a schematic view of an implant composition of one embodiment of the present invention immediately after introduction into a recipient site, showing the heterogeneous solid implant composition.

In one aspect of the present invention, an implant composition having controlled resorption rate comprises a calcium sulfate compound, polymer containing particles, and a setting agent for setting the calcium sulfate compound and the polymer containing particles into a heterogeneous solid composition. Upon setting, the calcium sulfate compound forms a matrix (M) and the polymer containing particles (P) settled within the matrix. FIG. 1 shows a cross-sectional schematic view of the heterogeneous solid implant composition before resorption occurs.

In another aspect, the present invention comprises a method of using implant materials to make the inventive implant composition for bone augmentation and bone defect reparation. The method comprises the steps of: (a) mixing a calcium sulfate compound and polymer containing particles with a setting agent into a mixture, (b) filling a recipient site with the mixture, and (c) setting the mixture into a heterogeneous solid composition.

The calcium sulfate compound is dry powder of calcium sulfate hemihydrate. Suitable setting agents include water, alkaline metal salt solutions such as a saline solution, and an accelerant aqueous solution containing potassium salt. The setting agents set the implant materials into a heterogeneous solid composition, or a multiphasic cement with different speeds. The speed of setting can be controlled from seven minutes to one hour, depending on the setting agent used as well as desired surgical application. Among various setting agents, potassium salt solutions result in the fastest setting. For the purpose of the present invention, an aqueous solution containing potassium or sodium ions are preferably used. Most preferably, an aqueous solution containing potassium ions can be used. Suitable examples of potassium salts include potassium sulfate, potassium phosphate, and potassium fluoride. The concentration of potassium ion controls the speed of setting, the higher it is the faster the setting process. Preferably, the concentration of the potassium ions is in a range from about 0.01 molar to about 0.5 molar.

The polymer containing particles (P) comprises a calcium sulfate compound, and at least one resorbable polymer. The calcium sulfate compound in the polymer containing particles can be calcium sulfate dihydrate, also called preset calcium sulfate, or calcium sulfate hemihydrate, also called unset calcium sulfate, or a mixture thereof. In one embodiment, the calcium sulfate compound is mixed with a resorbable polymer to form the particles. The amount of resorbable polymer used in the particles controls resorption rate of the implant composition when it is implanted in a recipient site. In an alternative embodiment, the calcium sulfate compound of the particles is encapsulated in a coating (C) of a resorbable polymer, as shown in FIG. 1. In this case, thickness of the resorbable polymer coating controls resorption rate of the implant composition in a recipient site. The thickness of the resorbable polymer coating is from about 2 μm to about 50 μm. For polymers that are only expected to last for a short time, a thin layer can be applied. For fast-resorbing coatings, or coatings expected to last for a long time, a thick coating can be applied. Furthermore, the resorbable polymer coating is not required to be a complete encapsulation. It has been observed that small local incomplete coatings, or coatings with defects (accidentally or intentionally), function as initial resorption sites of the polymer containing particles. An analogous situation can be found in time release medicine. It is known that medical pills with small controlled defects (drilled or molded) in polymer coatings are sometimes used to control drug release rates. A broad range of particle sizes can be used in the implant composition. The particle size can be determined depended on a particular application, and recipient site. For example, small particles are more suitable for dental fillings. On the other hand, larger pallets are more suitable for repairing bone fracture. Preferably, the particle size is more than 20 μm in diameter since when the particles are smaller than 20 μm, they may cause a negative foreign body response due to activation of macrophages.

In an additional embodiment, the particles can be made having combined characteristics of the two types of particles described above. Herein, the particles can include mixed calcium sulfate compound and a resorbable polymer, which are, additionally, encapsulated with a resorbable polymer coating.

In a further embodiment, the implant composition comprises two different types of polymer containing particles that have different rates of resorption. Such particles can, for example, be particles coated with different polymers, combinations of coated and mixed polymers, or particles with coating of different thickness, a typical range being 0.5 to 100 micrometers.

A wide variety of resorbable polymers can be used for the implant composition of the present invention. Suitable resorbable polymers include aliphatic polyesters of alpha-hydroxy acid derivatives, such as polylactides, polyglycolides, polydioxanone, and poly ε-caprolactone; hydrophobic polymers, such as carnuba waxes and their derivatives; water soluble polymers, such as tyrosine derived polycarbonates; and therapeutic polymers, such as those containing salicylate. A specific type of resorbable polymer can be selected depending on the purpose of applications, expected bone growth speed of a particular surgical site, and environment or condition of a recipient site.

In one preferred embodiment, polylactides and polyglycolides are used. It is known that polylactides, including D and L isomers, and DL copolymers of polylactic acid, have a long time history in their use as biomedical devices. In another preferred embodiment, poly(desaminotyrosyl-tyrosine alkyl ester carbonates) are used, wherein the alkyl group having one to ten carbon atoms. Suitable examples include, but are not limited to, poly(desaminotyrosyl-tyrosine ethyl ester carbonates), poly(desaminotyrosyl-tyrosine butyl ester carbonates), poly(desaminotyrosyl-tyrosine hexyl ester carbonates), and poly(desaminotyrosyl-tyrosine octyl ester carbonates). In short, they are referred to as poly (DTE carbonate), poly (DTB carbonate), poly (DTH carbonate), and poly (DTO carbonate), respectively. These polymers and polyglycolides are readily available commercially.

In general, resorbable polymers resorb slower in vivo than calcium sulfate compounds. Therefore, the amount of resorbable polymer used in the particles, mixed or coated, controls resorption rate of the implant composition when it is implanted in a recipient site. The polymer containing particles can comprise about 0.1% to about 50% (w/w) of a resorbable polymer, with about 1.5% defining the best mode. When the amount of a resorbable polymer is too high, it may cause a negative body, that is, immune response. When used as a coating only, the above (w/w) range is about 0.1% to about 22%. The rate of resorption of the implant composition can be controlled of between three (3) and twenty eight (28) weeks, depending on the types and amount of polymers used.

In an additional embodiment, the present invention relates to a method of preparing the polymer containing particles. The polymer containing particles can be prepared by two methods: (1) a surface coating process, and (2) bulk mixing of polymer and calcium sulfate. In the surface coating process, preformed calcium sulfate particles are mixed with a polymer solution. The polymer solution forms a liquid coating on the calcium sulfate particles, and is allowed to dry and to form a polymer surface coating on the particles. The coating thickness and amount of penetration into the calcium sulfate depend on the concentration of polymer in the solution, and viscosity of the solution. Examples of suitable organic solvent can be used to dissolve the polymer and make the polymer solution include acetone and chloroform. In the bulk mixing method, a fine granular form of a polymer is mixed with a granular form of calcium sulfate. The mixture is then pressed or rolled into larger particles.

Figure 2:
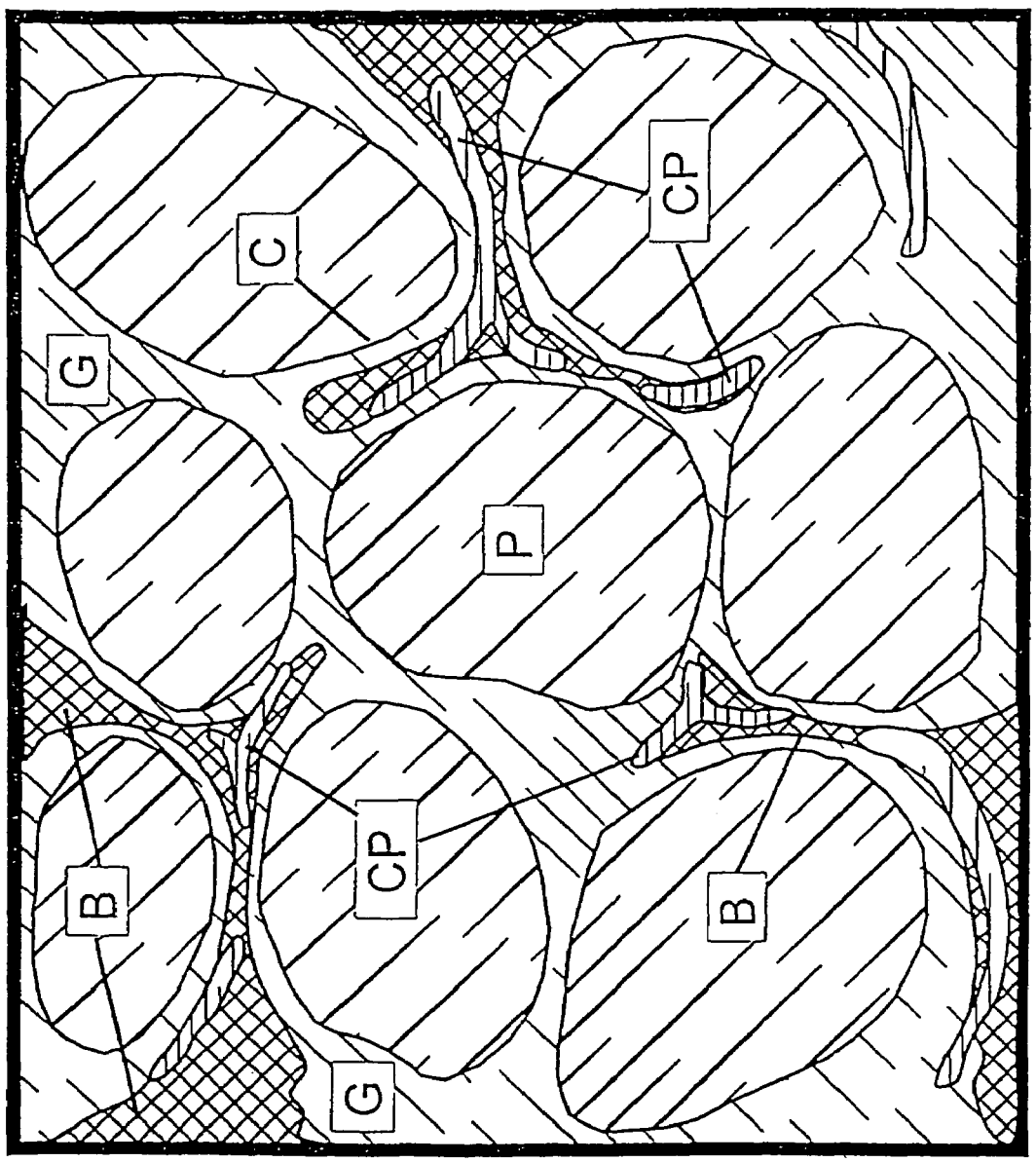
FIG. 2 is a view, sequential to that of FIG. 1, showing a first phase of bioresorption of the implant composition at the recipient site.

FIG. 1 to FIG. 4 illustrate the resorption process of the implant composition of the present invention, and the mechanism of controlled resorption rate for a proper stimulation of bone growth. FIG. 1 shows the structure of the heterogeneous solid implant composition after the mixture of calcium sulfate compound, polymer encapsulated particles, and the setting agent is being applied in a recipient site, and set into a heterogeneous solid composition. FIG. 2 shows the first phase of bioresorption of the implant composition. The calcium sulfate compound in the matrix resorbs first, that is, the first two to four weeks after implantation, thereby forming a porous system which will fill with granulation tissue (G) during said timeframe. The process of resorbing calcium sulfate forms deposits of calcium phosphate (CP) which has function to encourage early bone ingrowth (B).

Figure 3:
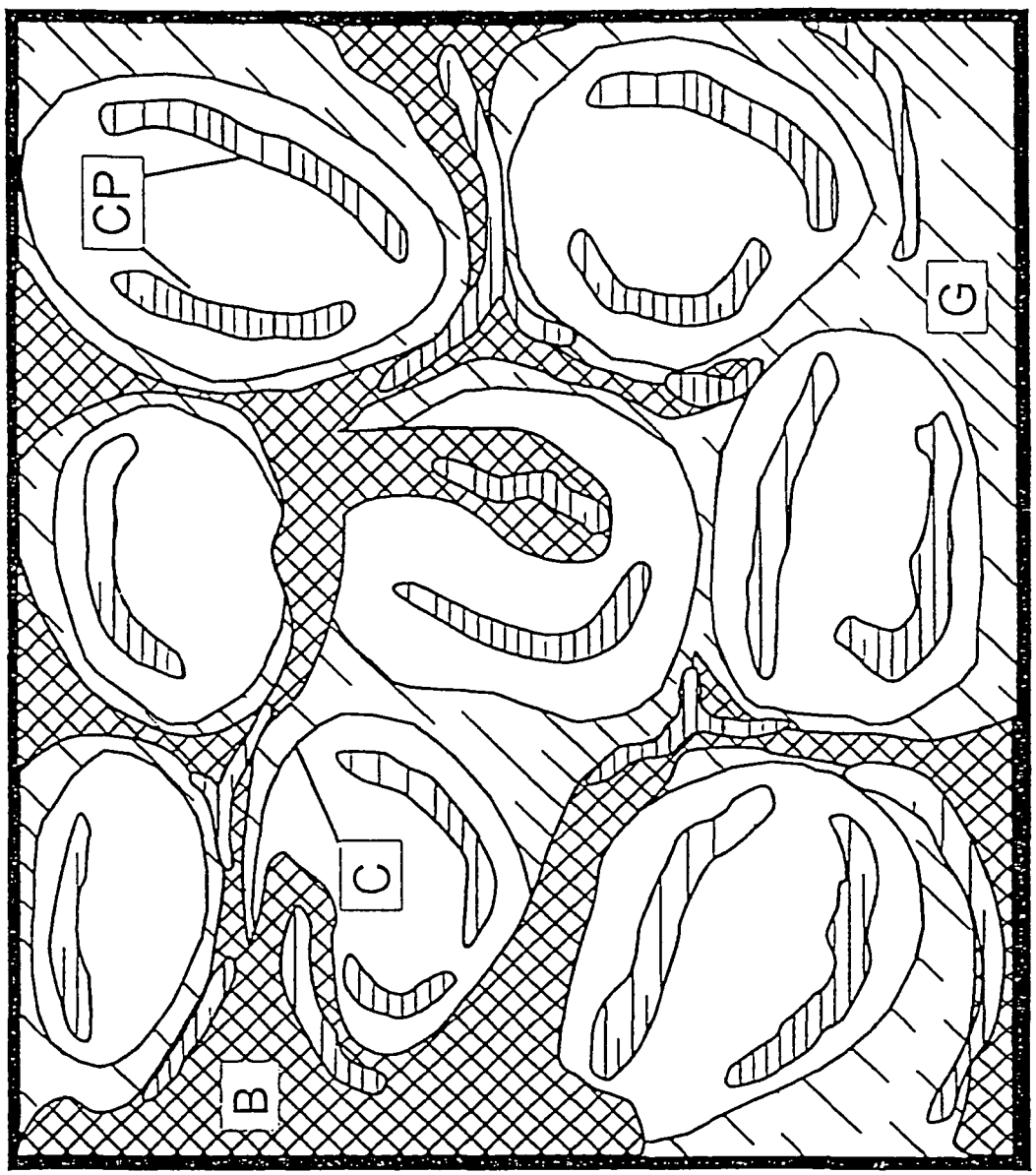
FIG. 3 is a view sequential to that of FIG. 2 showing the beginning of resorption of the polymer containing particles of the implant composition.

FIG. 3 shows the second phase of the resorption, i.e., resorption of the polymer containing particles. This occurs as early as four weeks or as late as twenty weeks after applying the implant composition, depending upon the particular formulation of the composition and application. In the example, as reflected in FIG. 3, the polymer coating has partially broken down allowing resorption of the encapsulated calcium sulfate compound. Therein, the resorbing calcium sulfate compound produces deposits of calcium phosphate (CP) as in the first phase of resorption (see FIG. 2), and additional bone ingrowth will occur.

Figure 4:
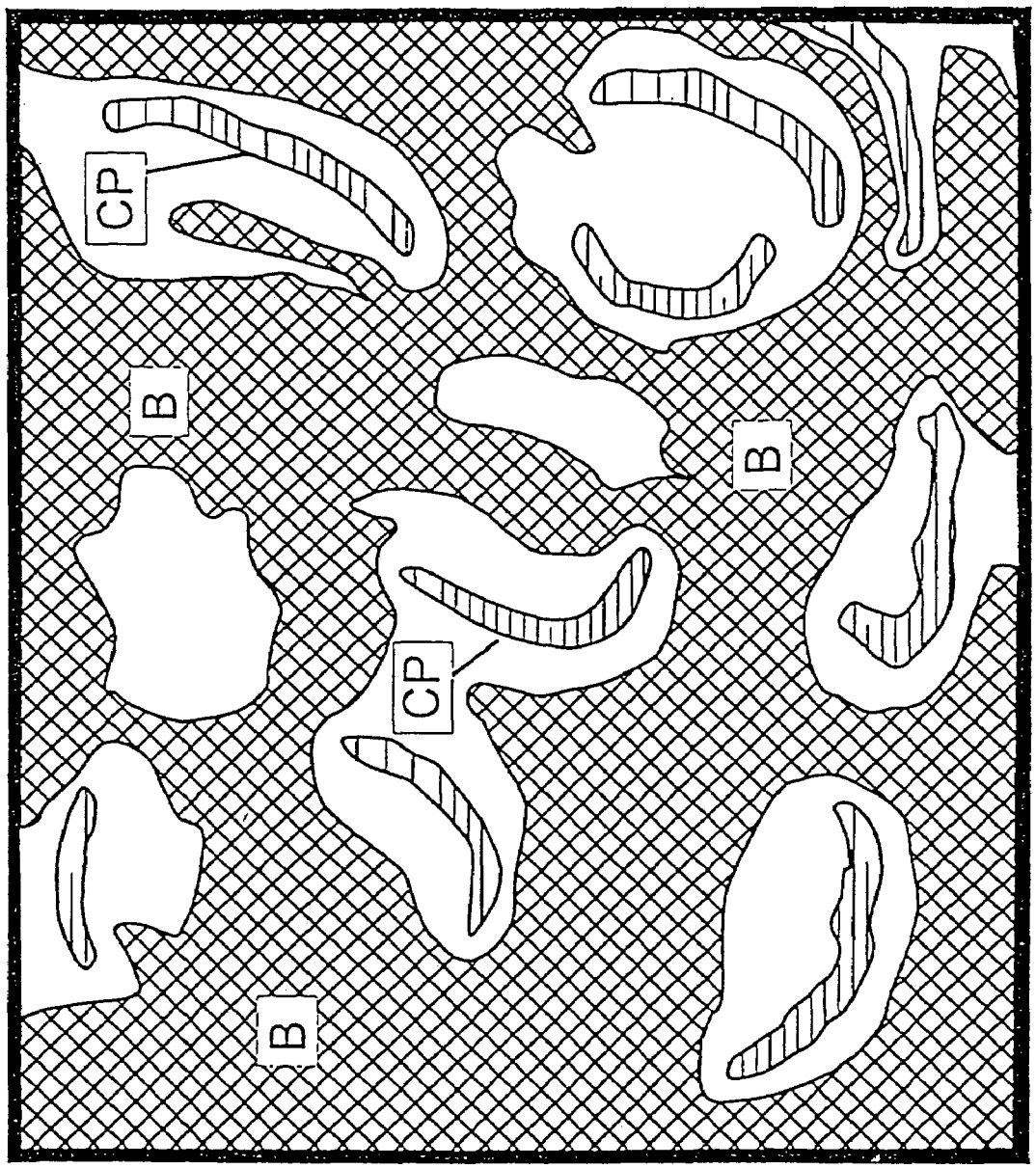
FIG. 4 is a view, sequential to that of FIG. 3, showing the end result of the bioresorption of the implant composition, which results stimulated bone growth with diminishing level of the implant composition.

FIG. 4 shows the end result of the resorption of the implant composition. This occurs as early as six weeks or as late as twenty four weeks depending upon the particular formulation of the composition and application. By this time only residual amount of polymer material remains and full bone ingrowth has occurred. In addition, most calcium phosphate deposits have been removed by bone remodeling, only a small amount of calcium phosphate deposits within the original particles can still be visible in new bone growth. It is understood that bone remodeling is a natural process that normally occurs very slowly. Remodeling occurs as new bone is constantly formed by osteoblasts and removed by osteoclasts. The balance of the two processes represents an equilibrium that determines how much bone is present at any given time. However, remodeling is rapid during healing, and virtually all of the immature bone that is formed during early healing is remodeled and replaced by more mature bone. The calcium phosphate deposits formed by the dissolving calcium sulfate are similar to bone mineral, and are also remodeled and replaced by more mature bone during this period of time.

The implant composition of the present invention can be used for the repair, augmentation, and other treatment of bone. The implant composition possesses significant advantages over existing calcium sulfate cements and pellets used clinically for bone repair and regeneration. More particularly, current calcium sulfate materials are resorbed by human bone within two to seven weeks, depending upon the calcium sulfate form and the particular surgical site, however, cannot be retained at the site for longer periods. As noted, such material is resorbed faster than it can be replaced by new bone thereby reducing its value to both patient and practitioner. The implant composition of the present invention can be designed to resorb in phases in accordance with the needs of a specific surgical application and environment of a recipient site, therein allowing substantial control of resorption rate. The resorption rate can be controlled of between eight and twenty four weeks, which substantially matches the rate of bone growth.

On the other hands, since methods involving separate use of calcium sulfate and polymeric components have long been established as safe and fully bioresorbable, clinical utilities and feasibility of the present invention are apparent. In particular, the implant composition of the present invention can be applied in dentistry for bone repairing and augmentation with or without a surgical implant.

Figure 5:
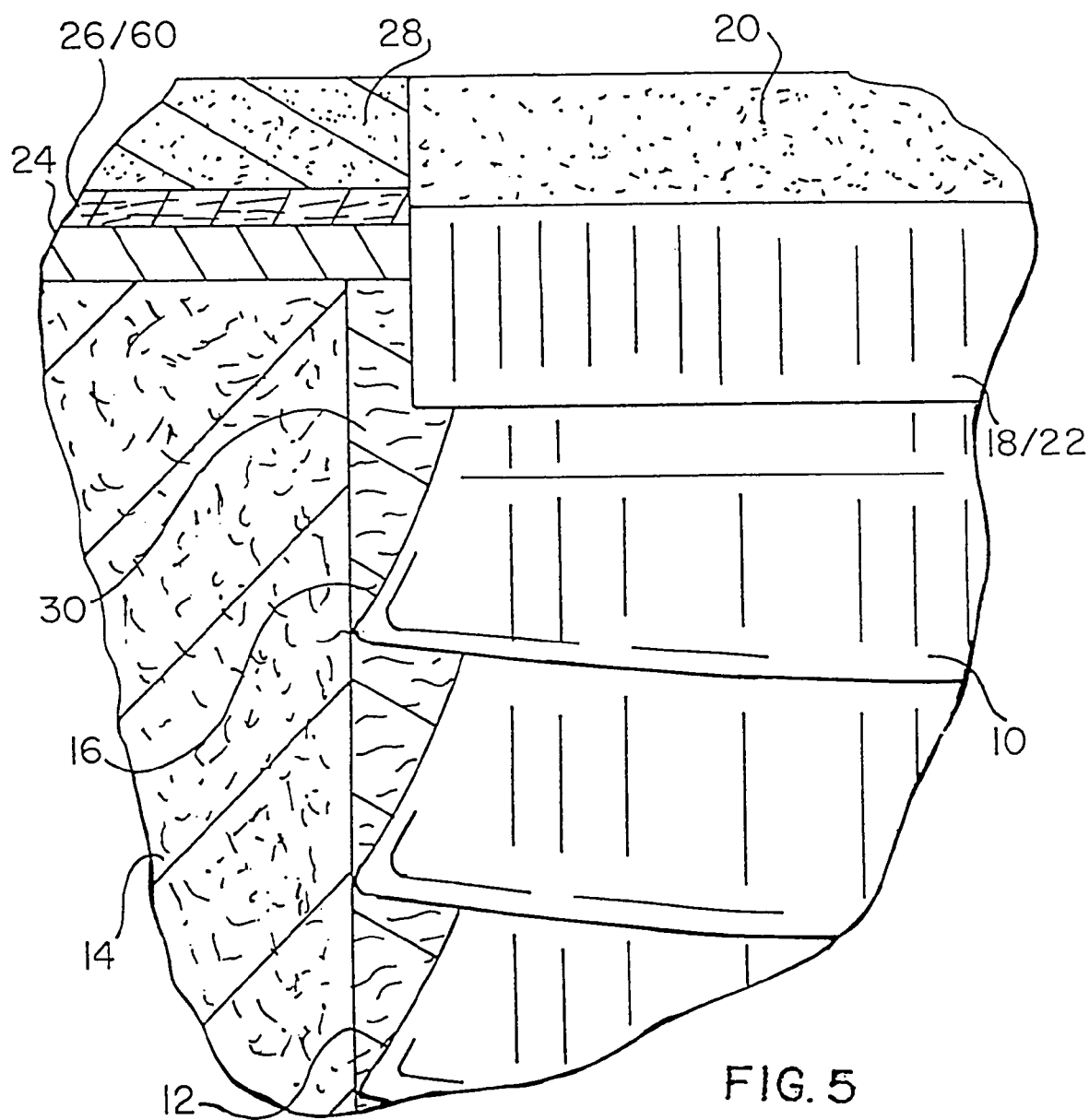
FIG. 5 is a cross-sectional schematic view of the implant composition of the present invention used with a surgical implant which has buttress threads.

FIG. 5 shows an example of using the implant composition of the present invention with a surgical implant. As shown, a surgical implant 10 is furnished at a surgical site 12 for the purpose of establishing bio-integration with surrounding bone tissue 14. An implant of the type of implant 10 includes buttress treads 16 (or other threading) and an integral collar 18 which comprises an upper part 20 and a lower part 22. Located above bone tissue 14 is a cortical bone layer 24, an optional bio-resorbable barrier layer 26 (described below) and a gum or soft tissue layer 28. The implant composition 30 of the present invention is filled in between bone tissue 14 and surgical implant 10 as an osseo-stimulative. It is to be understood that the implant composition can be applied to implant 10 before insertion into the osseotomy site or can be applied to the site 12, prior to insertion of the implant. Further, any of the surfaces of implant 10 inclusive of parts 20 and 22 of the collar 18 can be provided with cell growth stimulative microgeometry in accordance with our co-pending application Ser. No. 09/500,038. When a surgical implant exhibits an entirely smooth external geometry, as is the case with an implant 50 in FIG. 6, an osseo-stimulative surface 52 (FIG. 7) made of the implant composition of the present invention is more suitable when physically adhered to the implant at a pre-operative site. It is, however, to be appreciated that a paste of the implant composition can be applied to an osseotomy site in combination with use of implant 50 and its osseo-stimulative surface 52.

The implant materials of the present invention can be sold as a kit. The kit can comprise dry powder of calcium sulfate compound, one or more types of polymer containing particles. The kit can further comprise a setting agent packed in a container. The kit can also include instructions on how to prepare the implant mixture, apply it in a recipient site and set it into the solid implant composition.

While there has been shown and described the preferred embodiment of the instant invention it is to be appreciated that the invention may be embodied otherwise than is herein specifically shown and described and that, within said embodiment, certain changes may be made in the form and arrangement of the parts without departing from the underlying ideas or principles of this invention as set forth herewith.

What is claimed is:

1. Polymer containing calcium sulfate particles as an implant material, comprising a calcium sulfate compound selected from the group consisting of calcium sulfate dihydrate, calcium sulfate hemihydrate and a combination thereof, coated with at least one resorbable polymer consisting of polymer containing salicylate, with a coating thickness from about 2 µm to about 50 µm.

2. The polymer containing calcium sulfate particles of claim 1, wherein said polymer containing salicylate is in a range from about 0.1% to about 22% (w/w).

3. The polymer containing calcium sulfate particles of claim 1, wherein resorption of said particles in a recipient site is from about four weeks to about twenty weeks.

4. The polymer containing calcium sulfate particles of claim 1, wherein said particles are further coated with another resorbable polymer.

5. The polymer containing calcium sulfate particles of claim 4, wherein said another resorbable polymer is an aliphatic polyester of alpha-hydroxy acid derivatives.

6. The polymer containing calcium sulfate particles of claim 5, wherein said aliphatic polyester of alpha-hydroxy acid derivatives is a polylactide.

7. The polymer containing calcium sulfate particles of claim 5, wherein said aliphatic polyester of alpha-hydroxy acid derivatives is polyglycolide, polydioxanone, or poly ε-caprolactone.

8. The polymer containing calcium sulfate particles of claim 4, wherein said another resorbable polymer is a poly (desaminotyrosyl-tyrosine alkyl ester carbonate).

9. The polymer containing calcium sulfate particles of claim 8, wherein said poly(desaminotyrosyl-tyrosine alkyl ester carbonate) is poly(desaminotyrosyl-tyrosine ethyl ester carbonates), poly(desaminotyrosyl-tyrosine butyl ester carbonates), poly(desaminotyrosyl-tyrosine hexyl ester carbonates), or poly(desaminotyrosyl-tyrosine octyl ester carbonates).

\* \* \* \* \*